| United States Patent [19] | [11] Patent Number: 4,727,070 |
| Kaplan et al. | [45] Date of Patent: Feb. 23, 1988 |

[54] 3-PROPENZL CEPHALOSPORIN ISOMER SEPARATION PROCESS AND DERIVATIVE

[75] Inventors: Murray A. Kaplan; Michael W. Lovell, both of Syracuse; Joseph B. Bogardus, Manlius, all of N.Y.

[73] Assignee: Bristol-Myers Company, New York, N.Y.

[21] Appl. No.: 801,272

[22] Filed: Nov. 25, 1985

[51] Int. Cl.$^4$ .................. A61K 31/545; C07D 501/12
[52] U.S. Cl. .................................... 514/202; 540/215; 540/220; 540/222
[58] Field of Search ............................ 544/22, 20, 16; 514/202

[56] References Cited

U.S. PATENT DOCUMENTS

| 4,339,575 | 7/1982 | Ko'Oka et al. | 544/20 |
| 4,473,567 | 9/1984 | Ko'Oka et al. | 544/20 |
| 4,520,022 | 5/1985 | Hoshi et al. | 514/200 |

*Primary Examiner*—Donald G. Daus
*Assistant Examiner*—Barbara Cassatt
*Attorney, Agent, or Firm*—Robert E. Carnahan

[57] ABSTRACT

The antibiotic 7-[D-2-amino-2-(4-hydroxyphenyl)acetamido]-3-[(Z)-1-propenyl]ceph-3-em-4-carboxylic acid (BMY-28100) forms imidazolidinone derivatives on reaction with ketones. These derivatives are useful in pharmaceutical dosage forms and as intermediates for separation thereof from mixtures containing the [(E)-1-propenyl]isomer of the antibiotic.

21 Claims, 1 Drawing Figure

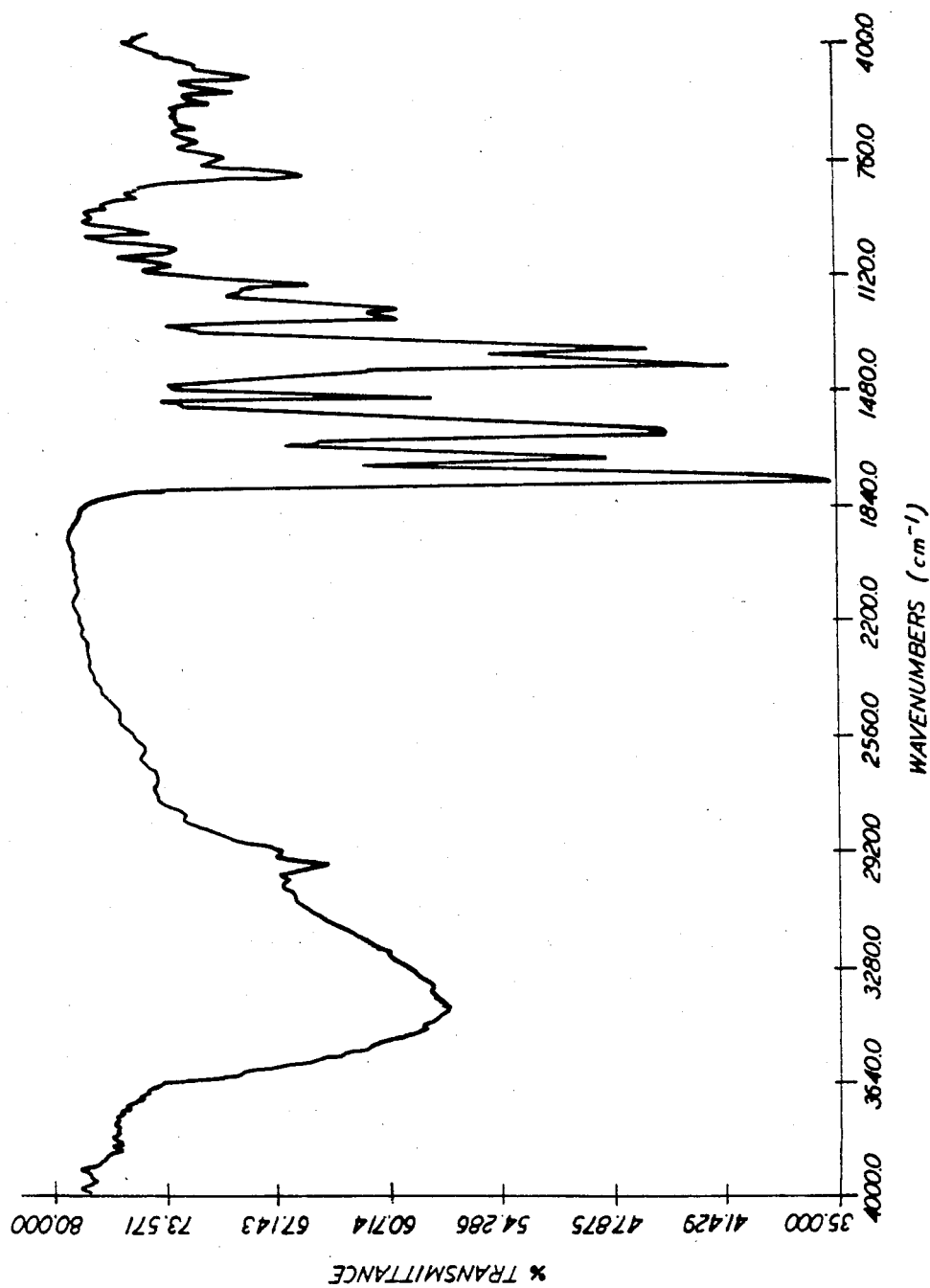

3-PROPENZL CEPHALOSPORIN ISOMER SEPARATION PROCESS AND DERIVATIVE

FIELD OF THE INVENTION

This invention relates to cephem compounds which contain an additional heterocyclic ring in the 7-position (Class 544, Subclass 25) which are derivatives of the cephalosporin antibiotic 7-[D-2-amino-2-(4-hydroxyphenyl)acetamido]-3-[(Z)-1-propenyl]ceph-3-em-4-carboxylic acid (BMY-28100).

Definition of Terms

The following terms are used in the present specification and claims.

antibiotic

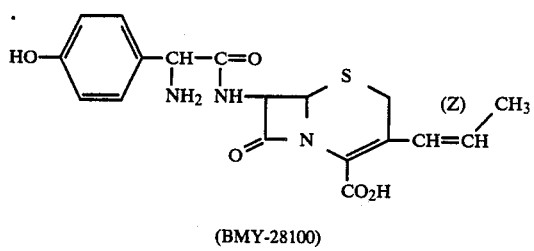

(BMY-28100)

(E)-isomer

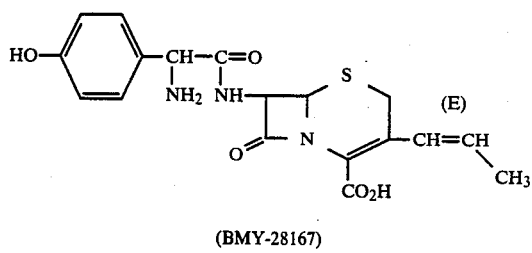

(BMY-28167)

antibiotic sodium salt
sodium 7-[D-2-amino-2-(4-hydroxyphenyl)acetamido]-3-((Z)-1-propenyl)ceph-3-em-4-carboxylate
(E)-isomer sodium salt
sodium 7-[D-2-amino-2-(4-hydroxyphenyl)acetamido]-3-((E)-1-propenyl)ceph-3-em-4-carboxylate
antibiotic sodium salt imidazolidinone derivative

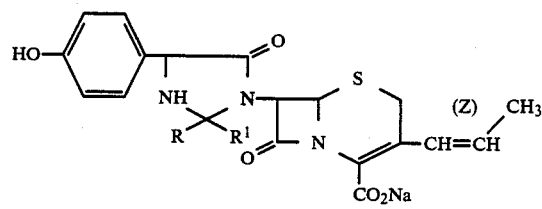

R and $R^1$ are alkyl, alicyclic, aryl, or aralkyl groups of the ketone having the formula

or they are joined to form a cyclic ketone, said ketone having a molecular weight of less than 200
(E)-isomer sodium salt imidazolidinone derivative

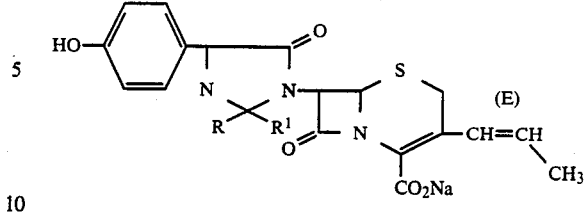

R and $R^1$ are the same as defined above.

The imidazolidinone derivatives pictured above when R and $R^1$ are methyl groups are sometimes referred to as acetonides.

DESCRIPTION OF THE PRIOR ART

The antibiotic BMY-28100 and its (E)-isomer BMY-28167 are described in U.S. Pat. No. 4,520,022 of Hoshi et al. patented May 28, 1985. These substances are produced synthetically according to methods which involve formation of the 3-(1-propenyl) group via the reaction of acetaldehyde with phosphoranyl intermediates prepared from 3-halomethyl cephalosporin starting materials. This type of synthesis is known as a Wittig synthesis, and in the present instance produces mixtures of the cis and trans-isomers about the propenyl double bond. The cis-isomer is referred to as the (Z)-isomer and the trans-isomer is referred to as the (E)-isomer. The (Z)-isomer is the desired form because of the improved Gram-negative antibacterial activity thereof compared to the (E)-isomer. For pharmaceutical purposes, it is desired to employ the (Z)-isomer substantially free of the (E)-isomer in order to secure the maximal antibiotic effect. By "substantially free" is meant no more than 2% by weight of the (E)-isomer.

Thus the problem presented to the art is to recover BMY-28100 from compositions containing it in admixture with the (E)-isomer thereof. Procedures 8 and 9 appearing at columns 20 and 21, of the Hoshi et al patent illustrate a preparative high performance liquid chromatography (HPLC) procedure for recovery of the antibiotic substantially free of the (E)-isomer from a composition containing the antibiotic and (E)-isomer in admixture. High performance liquid chromatography is not suited for large scale production of clinical and commercial quantities of an antibiotic such as this. Other conventional physical methods for separating mixtures of geometric isomers about an olefinic double bond have been unsuccessful with BMY-28100 containing mixtures such as fractional recrystallization, and selective absorption techniques.

Imidazolidinone derivatives of the type provided by the present invention have been prepared previously with cephalosporin and penicillin antibiotics having an α-amino-α-phenylacetamido substituent in the 7-position. Refer for instance to U.S. Pat. No. 3,198,804 and to G. A. Hardcastle et al. J. Org. Chem., 31, 897 (1966) which deal with derivatives of ampicillin which serve as prodrugs and are administered for therapeutic purposes. The antibiotic per se is released in the body. U.S. Pat. No. 3,994,884 to Weir discloses similar derivatives of cephalosporins having a vinyl group in the 3-position, and British Specification No. 1503310 refers to such derivatives of cefatrizine. Also, U.S. Pat. No. 4,026,688 of M. Kaplan et al. discloses oxazolidinone derivatives of cefatrizine with various aromatic aldehydes. There has, however, been no application of such derivatives to the separation of mixtures of cephalosporins where geometric isomerism about a double bond exists.

The matter of controlling the proportions of cis and trans olefins produced in the Wittig reaction with aldehydes has been studied by H. O. House et al. Journal of Organic Chemistry, 29, 3327-3333 (1964) with respect to the effect of solvents and various additives on the course of the reaction.

SUMMARY OF THE INVENTION

The present invention provides a 3-[(Z)-1-propenyl]-cephalosporin imidazolidinone carboxylic acid derivative having the following formula, a pharmaceutically acceptable metal or amine salt thereof, and a crystalline solvate of said acid or said salt with a pharmaceutically acceptable liquid.

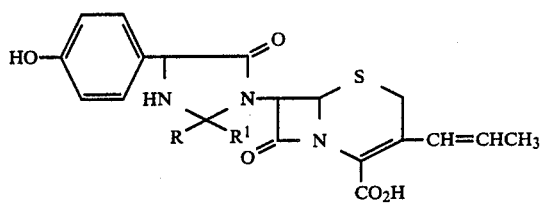

In the foregoing formula R and $R^1$ are the organic groups of an alkyl, alicyclic, aryl, or aralkyl ketone having the formula

$RCR^1$ and a molecular weight of up to 200. R and $R^1$ may be the same or different in any given instance. They are independently selected from alkyl, alicyclic, aryl, and aralkyl groups. They may be joined to form an alicyclic ketone such as cyclohexanone, cyclohexenone, or cyclopentanone. The preferred compounds are those wherein at least one of R and $R^1$ is alkyl having up to 4 carbon atoms, or they are joined to form a 6-membered ring. The most preferred compounds are those wherein R and $R^1$ are each methyl.

These compounds are of particular interest as intermediates in a purification process for the preparation of the antibiotic in its cis or (Z)-configuration substantially free of the (E)-isomer thereof. Synthetic processes for the production of the antibiotic generally yield mixtures containing both the (Z) and (E)-isomers whereas for pharmaceutical purposes it is (Z)-isomer that is desired. It has been found that the antibiotic sodium salt imidazolidinone derivatives are substantially insoluble in various organic solvents while the corresponding (E)-isomer sodium salt imidazolidinone derivatives are soluble. This affords the opportunity to separate the desired (Z)-configuration antibiotic as the crystalline sodium salt of the derivative pictured above from which the antibiotic per se may be regenerated or released.

These substances may be prepared as a pharmaceutically acceptable metal or amine salt. They are frequently isolated as crystalline solvates in which the crystal contains a definite proportion of the liquid from which it was crystallized. By solvate is meant a crystalline compound containing a definite proportion of solvent in the crystal lattice, usually the crystalline structure which can be characterized by X-ray powder diffraction spectrometry. They are stable solids at room temperature. The preferred compound of the present invention corresponds to the above formula wherein R and $R^1$ are each methyl groups, and the substance is isolated as the sodium salt monohydrate which is a crystalline solid.

The foregoing substances are prepared from the antibiotic BMY-28100 by conversion thereof to an alkali metal salt in the presence of a ketone as identified above. The products are isolated as the alkali metal salt. The pharmaceutically acceptable metal and amine salts are useful as dry pharmaceutical compositions because of their solid state stability. Those which are water soluble are particularly adapted for the preparation of parenteral dosage forms. They are transformed by hydrolysis or enzymatically in the body into the antibiotic BMY-28100. Hydrolysis occurs under conditions of acid pH such as pH 3–7 which are found in various mammalian tissues or organs. Strong aqueous acid (pH≦1) converts the metal and amine salts into the water insoluble acid form of the oxazolidinone products of the present invention.

DESCRIPTION OF THE DRAWING

The accompanying FIGURE is an illustration of the infra red absorption spectrum of a product of the present invention prepared according to Example 1. The crystalline sample was formed into a pellet using crystalline potassium bromide as carrier for the measurement.

DETAILED DESCRIPTION OF THE INVENTION

The process of the present invention is applicable to antibiotic BMY-28100 compositions containing from 2% to about 65% by weight of the (E)-isomer thereof. Compositions containing 2% or less of the (E)-isomer are regarded as substantially free of the (E)-isomer for pharmaceutical purposes. It is the preparation of antibiotic BMY-28100 compositions which are substantially free of the (E)-isomer which is one object of the present invention. Another object is the provision of antibiotic BMY-28100 prodrug derivatives which are particularly adapted for pharmaceutical dosage compositions.

The process of the present invention involves first contacting an antibiotic BMY-28100 composition containing from 2% to about 65% by weight of the (E)-isomer with a sodium salt-forming reagent in the presence of the ketone reagent

$RCR^1$.

The sodium salt of an acid which is a weaker acid than the antibiotic, or its (E)-isomer is preferably used as sodium salt-forming reagent. This is preferably carried out in solution and it is desirable to select solvents and salt-forming reagents for the first step which result in the formation of a solution at the outset or as the reaction proceeds. As the imidazolidinone derivatives are formed, precipitation of the antibiotic sodium salt imidazolidinone derivative occurs due to the lower solubility thereof relative to the (E)-isomer sodium salt imidazolidinone derivative. After completion of the reaction, the antibiotic sodium salt imidazolidinone derivative is recovered by filtration or centrifugation. The resulting product is useful per se for pharmaceutical purposes or may be transformed into the antibiotic per se which is substantially free of the (E)-isomer thereof.

In carrying out the foregoing process, it is preferred to use sodium 2-ethylhexanoate as salt-forming reagent, but other reagents such as sodium acetate or the sodium salt of other carboxylic acids may be employed. A reaction inert organic solvent such as a liquid alkanol or ester, is preferably employed in combination with the ketone used as imidazolidinone-forming reagent as solvent. A minimal quantity of water may also be employed to facilitate dissolution. The preferred solvents are mixtures of methanol and acetone. The acetonides of BMY-28100 and BMY-28167 are very soluble in methanol, and substantially insoluble in acetone. Accordingly mixtures of these two solvents are employed to provide the desired differential solubility. Mixtures of methanol and acetone containing from 20% to 50% by volume of methanol are suitable. The antibiotic sodium salt 2,2-dimethylimidazolidinone derivative is insoluble in the methanol-acetone mixture at room temperature or below while the 2,2-dimethylimidazolidinone derivative sodium salt of the (E)-isomer is soluble. This difference in solubility provides a basis for the separation of these, otherwise very similar materials.

The foregoing process will take place at room temperature, but it is preferred to employ a somewhat elevated temperature since solubilities of the reactants are increased, and the reaction rate is accelerated. The optimal temperature may be determined with a minimum of experimentation having consideration for the stability of the antibiotic and losses resulting from decomposition thereof at elevated temperatures, as well as the crystal form of the product produced. When using methanol and acetone, according to the preferred embodiment of the present invention, a temperature of 35 to 55 deg. C. is preferred. The product crystallizes in a more manageable form at temperatures of 40 to 55 deg. C.

Where alkyl, aryl, or aralkyl ketones are employed which are not suitable solvent materials for the antibiotic and the (E)-isomer thereof, the ketone may be provided as a solute in an organic solvent in approximately chemically equivalent amount relative to the antibiotic and (E)-isomer thereof. In this instance, a solvent is selected in which the antibiotic sodium salt imidazolidinone derivative produced from this ketone is insoluble, while the (E)-isomer sodium salt imidazolidinone derivative is soluble. Testing of various combinations of ketones, salt-forming reagents, and solvents to accomplish this purpose is within the skill of the laboratory chemist.

The present process is applicable to antibiotic BMY-28100 compositions wherein solvated forms of the antibiotic and the (E)-isomer thereof are present. For instance, the process of the above cited U.S. Pat. No. 4,520,022 produces the crystalline monohydrate which is a suitable form for treatment according to the present invention. Another suitable form is the dimethylformamide solvate which is produced by the process of copending application Ser. No. 759,805 filed July 29, 1985, the disclosure of which is incorporated herein by reference.

Pharmaceutically acceptable metal and amine salts are those salts which are stable under ambient conditions, and in which the cation does not contribute significantly to the toxicity or biological activity of the salt. Suitable metal salts include the sodium, potassium, calcium, zinc, and magnesium salts. The sodium or potassium salts are highly water soluble and are preferred.

Amine salts prepared from amines used for instance with benzyl penicillin which are capable of forming stable salts with the acidic carboxyl group include trialkylamines such as triethylamine, procaine, dibenzylamine, N-benzyl-β-phenethylamine, 1-ephenamine, N,N'-dibenzylethylenediamine, dehydroabiethylamine, N-ethylpiperidine, benzylamine, and dicyclohexylamine. Some of these amine salts are insoluble in water.

The applicability of sodium 7-[2,2-dimethyl-4-(4-hydroxyphenyl)-5-oxo-1-imidazolidinyl]-3-[(Z)-1-propenyl]ceph-3-em-4-carboxylate as a solution dosage form for parenteral injection was demonstrated by preparation of an aqueous solution containing 250 mg/ml thereof, and measuring the concentration of antibiotic in solution at room temperature during a storage period of several hours. It was found that the solution having pH 7.2 lost 10% potency in approximately 2 hours. This is far superior stability to that demonstrated by the sodium salt of the antibiotic per se which exhibited pH 8.2 and lost 10% of its potency in 30 minutes. While 10% loss in potency is considered tolerable a sufficient so-called utility time of at least 2 hours is required for an extemporaneously prepared antibiotic solution.

The solid state stability of this substance was demonstrated by storing samples thereof at various temperatures for various periods of time and measuring the purity of the sample at different intervals. The results are summarized in the following table:

| Time | SOLID STATE STABILITY | |
| --- | --- | --- |
| | Temperature Deg. C. | % Remaining |
| 4 Weeks | 37 | 100 |
| 4 Weeks | 45 | 102 |
| 4 Weeks | 56 | 98.6 |
| 1 Week | 70 | 94.0 |
| 1 Day | 100 | 80.0 |

A further benefit of the present process is that the antibiotic recovered by hydrolysis of the antibiotic sodium salt imidazolidinone derivative is that colored impurities are reduced.

DESCRIPTION OF SPECIFIC EMBODIMENTS

EXAMPLE 1

Imidazolidinone Derivatives from Acetone

A solid composition comprised of 83% of the crystalline monohydrate of the antibiotic BMY-28100 and 17% of the (E)-isomer thereof (BMY-28167) and weighing 102 g was mixed with 2 liters of acetone and the slurry then warmed with stirring to 40 deg. C. With continued stirring 83.1 g (0.5 m) of sodium 2-ethylhexanoate in powder form was added followed by 1.2 liters of methanol. A clear solution formed within 5 minutes of continued stirring at 40 deg. C. After 15 minutes the sodium salt of the acetone imidazolidinone derivative of the antibiotic, viz. sodium 7-[2,2-dimethyl-4-(4-hydroxyphenyl)-5-oxo-1-imidazolinyl]-3-[1(Z)-propenyl]ceph-3-em-4-carboxylate began to crystallize. After 1 hour the mixture became very thick and 1 liter of 1:1 v/v methanol/acetone was added to facilitate mixing. After stirring for 1 additional hour at 40 deg. C. the mixture was cooled to 15–20 deg. C. with stirring and the insoluble product then recovered by vacuum filtration. The moist filter cake was suspended in the mixture of 2 liters of acetone and 0.5 liters of methanol and agitated for 1 hour at 20 deg. C. The product was collected by filtration, washed on the filter with 0.2 liters of 2:8 v/v methanol/acetone and then with acetone, and transferred to a vacuum desiccator and dried. A second crop was obtained by concentration of the filtrate to 0.5 liters and mixing the concentrate with 0.5 liters of acetone. This material was collected by filtration, resuspended in 1 liter of 1:5 v/v methanol/acetone, collected and dried to yield an additional 22.1 g of product equivalent in quality to the first crop. Total yield 86.1 g (93%).

Analytical Data:

A. Structure:

[Structure diagram showing: HO-phenyl-CH(NH-C(CH$_3$)$_2$CH$_3$)-C(=O)-N-(β-lactam ring with S)-C=C(CH$_3$)-CO$_2$Na, with labeled hydrogens H$^1$, H$^2$, H$^4$, H$^5$, H$^6$, H$^7$, H$^8$ and carbons CH$_3^3$, CH$_3^9$]

$C_{21}H_{22}N_3O_5SNa \cdot H_2O$
MW: 451.49

The product is obtained as a crystalline hydrate.
Elemental:

| Calc'd | | Found | |
|---|---|---|---|
| % C | 55.85 | % C | 55.50 |
| % H | 4.91 | % H | 5.00 |
| % N | 9.31 | % N | 8.89 |
| % S | 7.10 | % S | 6.83 |
| % KF(H$_2$O) | — | % KF(H$_2$O) | 4.58 |
| % sulfate ash | 5.09 | % sulfated ash (as Na) | 4.77 |

The infrared absorption spectrum is shown in the accompanying FIGURE. In the ultra violet, the following absorption is exhibited.

$\lambda_{max} = 222$ nm (E=14423)

Nuclear magnetic resonance

| Chemical Shift (relative to trimethylsilyl propane sulfonic acid 0. ppm in D$_2$O with water elimination) | | | |
|---|---|---|---|
| 7.35 | doublet | 2H's(aromatic) | H$^1$ |
| 6.95 | doublet | 2H's(aromatic) | H$^1$ |
| 6.0 | doublet | 1H(vinylic) | H$^7$ |
| 5.75 | multiplet | 1H(vinylic) | H$^8$ |
| 5.25 | singlet | 2 singlets | H$^2$, H$^4$, H$^5$ |
| 4.78 | singlet | 3H's | |
| 3.47 | doublet of doublets | 2H's | CH$_2^6$ |
| 1.65 | doublet | 3H's | CH$_3^9$ |
| 1.50 | singlet | 6H's | 2(CH$_3^3$) |

Other ketones such as cyclohexanone, methyl ethyl ketone, cyclopentanone, methyl vinyl ketone, and methyl isobutyl ketone may be substituted for acetone in the foregoing process.

EXAMPLE 2

Hydrolysis of Imidazolidinone Derivative to Antibiotic

The imidazolidinone derivative produced in Example 1, 30 g, was added as a dry powder to 175 ml of water, previously warmed to 40 deg. C. and contained in a reaction vessel equipped with a stirrer, thermometer, dropping funnel, and pH electrode. The pH of the reaction mixture rose as the acetone derivative dissolved and was maintained in the range of pH 5.8 to 6.0 by the dropwise addition of 1N HCl. After 15 minutes a second 30 g portion of the imidazolidinone derivative was added while maintaining the pH at pH 5.8–6.0. The final portion, 26 g, of the imidazolidinone derivative was added approximately 15 minutes after the second portion in the same fashion. The pH was monitored during a period of 4.5 hours and maintained at pH 5.8–6.0 by the addition of 1N HCl during this period. The mixture was then cooled to approximately 0 deg. C. and adjusted to pH 4.1 by the addition of 1N hydrochloric acid. After 20 minutes the product was collected by filtration, the filter cake washed with 100 ml of ice-cold water, and the filter cake dried in vacuo. Yield 62.4 g (83.6%). This material was shown by PMR to contain 1.5% by weight of the (E)-isomer, and by HPLC to be comprised of 94.9% by weight of the desired antibiotic (Z)-isomer and 1.78% by weight of the (E)-isomer.

The following system is suitable for the HPLC of the raw material for Example 1 and the product of Example 2 for proportions of the (Z) and (E) components (BMY-28100/BMY-28167).

OPERATING CONDITIONS (Column: Lichrosorb C-18, Cat. No. 218604)

Mobile phase:
  Pump A: 97.5 parts 0.1M NH$_4$H$_2$PO$_4$, pH 4.4, 2.5 parts acetonitrile
  Pump B: Acetonitrile Gradient:
  From 100% A to 75% A/25% B in 25 minutes, equilibrate column for 10 minutes Diluent:
  25% acetonitrile/water Injection volume:
  10 μl Flow:
  1.0 ml/min.

Detector:
  UV at 230 nm

Sample conc.:
  BMY-28100 composition at 2 mg/ml

Retention times:
  BMY-28100 = 11 minutes
  BMY-28167 = 13 minutes
  BMY-28100 acetonide = 17 minutes
  BMY-28167 acetonide = 19 minutes

EXAMPLE 3

Conversion of Antibiotic Sodium Salt Imidazolidinone Derivative with Sodium Bisulfite The product of Example 1, 125 mg, was dissolved in 1 ml of water at 45–50 deg. C. While stirring this solution, 62.5 mg (about 2.5 molecular equivalents) of sodium bisulfite was added during a 20 minute period. At this stage it is appropriate to add seed crystals of BMY-28100 monohydrate if available, but this is not essential. Heating and stirring are continued for one-half hour. The mixture is cooled to room temperature, kept for another half hour with stirring and the product is then collected. The yield is approximately 60% of BMY-28100 monohydrate containing 1.8% of the (E)-isomer thereof.

EXAMPLE 4

Acetone Imidazolidonone Derivative From BMY-28100 Dimethylformamide Solvate

Materials:
 4.62 g (0.0092 m) of BMY-28100·1.5 DMF
 3.32 g (0.02 m) of sodium 2-ethylhexanoate
 100 ml of acetone
 40 ml of methanol
 0.18 ml (0.1 m) water A slurry of the BMY-28100·1.5 DMF in the mixture of methanol and acetone was stirred at room temperature while the sodium 2-ethylhexanoate was added thereto followed by the water. The mixture with continued stirring was warmed to 40 deg. C. A clear solution formed within about 5 minutes. Approximately 10 minutes thereafter a precipitate commenced to form. The mixture was maintained at 40 deg. C. for 2½ hours with stirring and then cooled to about 18 deg. C., and the product collected. The product is substantially identical to that produced by Example 1.

EXAMPLE 5

Capsule Dosage Form

The following materials are blended in the dry state and then loaded into hard gelatin capsules to a fill weight of 0.345 g.
 302.5 g Sodium 7-[2,2-dimethyl-4-(4-hydroxyphenyl)-5-oxo-1-imidazolinyl]-3-[(Z)-1-propenyl]ceph-3-em-4-carboxylate hydrate (Example 1)
 2.0 g Magnesium stearate
 30.0 g Microcrystalline cellulose (Avicel PH 102)
 10.5 g Starch The batch is sufficient for 1000 capsules suitable for oral administration.

EXAMPLE 6

Solution for Injection

Example 1 is adapted to aseptic procedures to provide sterile crystalline sodium 7-[2,2-dimethyl-4-(4-hydroxyphenyl)-5-oxo-1-imidazolinyl]-3-[(Z)-1-propenyl]ceph-3-em-4-carboxylate. The latter has a water solubility of several hundred milligrams per milliliter, and accordingly, appropriate dosage amounts are readily soluble in the common aqueous injection vehicles such as water, glucose solution, normal saline, etc. As an example, 302.3 mg of sterile crystalline material can be distributed to individual vials which are capped with sterile rubber stoppers and sealed with aluminum seals. At the time of use, 2 to 3 ml of injection vehicle such as sterile water is injected into the vial and the injection solution then withdrawn into the syringe and administered by parenteral injection. The quantity of sodium 7-[2,2-dimethyl-4-(4-hydroxyphenyl)-5-oxo-1-imidazolinyl]-3-[(Z)-1-propenyl]ceph-3-em-4-carboxylate is the molecular equivalent of 250 mg of antibiotic BMY-28100.

EXAMPLE 7

Suppository Dosage Form

A batch of 100 suppositories suitable for rectal administration is prepared from the following ingredients.
 154.8 g of a hard friable low hydroxyl fat suppository base such as Witepsol H-15 (Dynamit-Nobel)
 30.23 g of sodium 7-[2,2-dimethyl-4-(4-hydroxyphenyl)-5-oxo-1-imidazolinyl]-3-[(Z)-1-propenyl]-ceph-3-em-4-carboxylate monohydrate The fatty base material is melted at 50-60 deg. C. and then cooled to just above its melting point (35 deg. C.) with moderate stirring. The imidazolinyl derivative is then scattered on the surface of the melted base until the entire amount has been distributed during a 15 minute interval. Stirring is continued for one hour and then the blend is poured into preheated suppository molds. The mold and contents are then allowed to cool to 22-26 deg. C. and the suppositories are removed and packaged. Each suppository contains a dose equivalent to 250 mg of the antibiotic BMY-28100.

We claim:

1. The process for preparing and separating antibiotic sodium salt imidazolidinone derivative which comprises (1) contacting a composition containing the antibiotic 7-[D-2-amino-2-(4-hydroxyphenyl)acetamido]-3-[(Z)-1-propenyl]ceph-3-em-4-carboxylic acid in admixture with the (E)-isomer thereof with a sodium salt forming reagent in the presence of an alkyl, alicyclic, aryl, or aralkyl ketone having a molecular weight of less than 200 under reaction conditions whereby antibiotic sodium salt imidazolidinone derivative and (E)-isomer sodium salt imidazolidinone derivative are formed (2) suspending the imidazolidinone derivatives formed in Step (1) in a solvent in which said (E)-isomer sodium salt imidazolidinone derivative is soluble and said antibiotic sodium salt imidazolidinone derivative is substantially insoluble thereby forming a suspension of said antibiotic derivative in a solution of said (E)-isomer derivative, and (3) recovering said insoluble antibiotic derivative from said suspension substantially free of said (E)-isomer derivative.

2. The process of claim 1 wherein in Step (1) said ketone is acetone.

3. The process of claim 1 wherein in Step (1) said sodium salt forming reagent is sodium 2-ethylhexanoate and said contacting is carried out in a liquid medium.

4. The process of claim 3 whereby during Step (1) a solution is formed.

5. The process of claim 3 wherein methanol and acetone are employed.

6. The process of claim 5 wherein said contacting is carried out at a temperature of 35-55 deg. C.

7. The process of claim 5 wherein said contacting is carried out at a temperature of 40-55 deg. C.

8. The process of claim 1 wherein the solvent in Step (2) is a mixture of methanol and acetone.

9. The process of claim 1 wherein said antibiotic derivative recovered in Step (3) is converted to 7-[D-2-amino-2-(4-hydroxyphenyl)acetamido]-3-[(Z)-1-propenyl]ceph-3-em-4-carboxylic acid substantially free of the E-isomer thereof.

10. The process of claim 1 wherein said antibiotic derivative recovered in Step (3) is sodium 7-[2,2-dimethyl-4-(4-hydroxyphenyl)-5-oxo-1-imidazolidinyl]-3-[(Z)-1-propenyl]ceph-3-em-4-carboxylate, or a crystalline hydrate thereof.

11. The process of claim 1 wherein the antibiotic composition treated in Step (1) comprises a crystalline solvate of said 7-[D-2-amino-2-(4-hydroxyphenyl)acetamido]-3-[(Z)-1-propenyl]ceph-3-em-4-carboxylic acid and the (E)-isomer thereof.

12. The process of claim 11 wherein said solvate is the hydrate.

13. The process of claim 11 wherein said solvate is the dimethylformamide solvate.

14. The 3-[(Z)-1-propenyl]cephalosporin imidazolidinone derivative having the formula

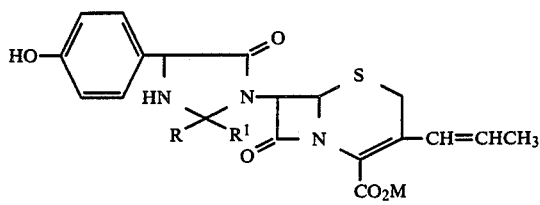

wherein R and R¹ are the organic groups of an alkyl, alicyclic, aryl, or aralkyl ketone having the formula

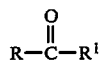

or they are joined to form a alicyclic ketone, said ketone having a molecular weight of up to 200, a pharmaceutically acceptable metal or amine salt thereof, or a crystalline solvate of said acid or said salt with a pharmaceutically acceptable liquid.

15. The compound of claim 14, 7-[2,2-dimethyl-4-(4-hydroxyphenyl)-5-oxo-1-imidazolinyl]-3-[(Z)-1-propenyl]ceph-3-em-4-carboxylic acid, a pharmaceutically acceptable metal or amine salt thereof, or a crystalline solvate of said acid or said salt with a pharmaceutically acceptable liquid.

16. The sodium salt of claim 15.

17. The sodium salt crystalline hydrate of claim 15.

18. A pharmaceutical composition comprising an antibiotically effective amount of a compound of claims 15, 16, or 17 and a carrier therefor.

19. The composition of claim 18 comprised of a solid dosage unit adapted for ingestion.

20. The composition of claim 18 comprised of a solution or suspension adapted for parenteral injection.

21. The composition of claim 18 comprised of a suppository.

* * * * *

UNITED STATES PATENT AND TRADEMARK OFFICE
CERTIFICATE OF CORRECTION

PATENT NO. : 4,727,070

DATED : February 23, 1988

INVENTOR(S) : Kaplan, Murray A. et al.

It is certified that error appears in the above-identified patent and that said Letters Patent is hereby corrected as shown below:

In the title the word "PROPENZL" should read

-- PROPENYL --.

Column 11, line 13: The portion of the structural formula in Claim 14 which reads "$\overset{|}{C}O_2M$" should be corrected to read -- $\overset{|}{C}O_2H$ --.

Signed and Sealed this

Nineteenth Day of July, 1988

Attest:

DONALD J. QUIGG

Attesting Officer

Commissioner of Patents and Trademarks